US008668901B2

(12) United States Patent
Muellinger et al.

(10) Patent No.: US 8,668,901 B2
(45) Date of Patent: Mar. 11, 2014

(54) USE OF A GLUCOCORTICOID COMPOSITION FOR THE TREATMENT OF SEVERE AND UNCONTROLLED ASTHMA

(75) Inventors: Bernard Muellinger, Munich (DE); Gerhard Scheuch, Wohrathal (DE); Thomas Hofmann, Doylestown, PA (US); Philipp Kroneberg, Olching (DE)

(73) Assignee: Activaero GmbH Research & Development, Gauting (DE)

(*) Notice: Subject to any disclaimer, the term of this patent is extended or adjusted under 35 U.S.C. 154(b) by 0 days.

(21) Appl. No.: 13/147,761

(22) PCT Filed: Feb. 3, 2010

(86) PCT No.: PCT/EP2010/051321

§ 371 (c)(1), (2), (4) Date: Oct. 19, 2011

(87) PCT Pub. No.: WO2010/089330

PCT Pub. Date: Aug. 12, 2010

(65) Prior Publication Data

US 2012/0040945 A1 Feb. 16, 2012

Related U.S. Application Data

(63) Continuation-in-part of application No. 12/365,754, filed on Feb. 4, 2009, now abandoned.

(51) Int. Cl.

| | |
|---|---|
| ***A01N 25/02*** | (2006.01) |
| ***A61K 9/12*** | (2006.01) |
| *A61K 9/14* | (2006.01) |
| *A01N 45/00* | (2006.01) |
| *A61K 31/56* | (2006.01) |
| *B05B 17/06* | (2006.01) |
| *A61M 16/00* | (2006.01) |

(52) U.S. Cl.

USPC ............... 424/43; 424/45; 424/489; 514/169; 514/170; 514/862; 514/958; 128/200.16; 128/200.21; 128/200.13; 600/538

(58) Field of Classification Search

USPC ............. 424/43, 45, 489; 514/169, 170, 862, 514/958; 128/200.16, 200.21, 203.13; 600/538

See application file for complete search history.

(56) References Cited

U.S. PATENT DOCUMENTS

| | | | | |
|---|---|---|---|---|
| 6,187,765 | B1 | 2/2001 | Harris et al. | |
| 6,401,710 | B1 | 6/2002 | Scheuch | |
| 6,463,929 | B1 | 10/2002 | Scheuch | |
| 6,571,791 | B2 | 6/2003 | Scheuch | |
| 6,606,989 | B1 * | 8/2003 | Brand et al. | 128/200.16 |
| 6,681,762 | B1 | 1/2004 | Scheuch | |
| 7,077,125 | B2 | 7/2006 | Scheuch | |
| 2001/0037806 | A1 | 11/2001 | Scheuch | |
| 2005/0087189 | A1 | 4/2005 | Crockford et al. | |
| 2006/0201499 | A1 | 9/2006 | Muellinger | |
| 2007/0006883 | A1 | 1/2007 | Kolb | |
| 2007/0020299 | A1 * | 1/2007 | Pipkin et al. | 424/400 |

FOREIGN PATENT DOCUMENTS

WO WO 2010043981 A1 4/2010

OTHER PUBLICATIONS

Powell et al., "High dose versus low dose inhaled corticosteroid as inititial starting dose for asthma in adults and children"; 2003; Cochrane Database of Systematic Reviews; Issue 4, No. CD004109.*

Scheuch et al., "Novel Approaches to Enhance Pulmonary Delivery of Proteins and Peptides," Nov. 1, 2007; J. of Physiology and Pharmacology; Polish Physiological Society, Krakow, PL; V58/suppl. 5(2): 615-625.*

Nelson et al., "Fluticasone propionate powder: oral corticosteroid-sparing effect and improved lung function and quality of life in patients with severe chronic asthma"; Feb. 1999; Allergy Clin. Immunol., 103(2 Pt. 1):267-275; Abstract.*

Nelson et al., "Fluticasone propionate powder: oral corticosteroid-sparing effect and improved lung function and quality of life in patients with severe chronic asthma"; Feb. 1999; Allergy Clin. Immunol., 103(2 Pt. 1): 267-275; Abstract.*

Scheuch et al., "Novel Approaches to Enhance Pulmonary Delivery of Proteins and Peptides," Nov. 1, 2007; J. of Physiiology and Pharmacology; Polish Physiological society, Krakow, PL; V58/supp. 5(2):615-625.*

Powell et al., "High dose versus low dose inhaled corticosteroid as initial starting dose for asthma in adults and children,"; 2003; Cochrane Database of Systematic Reviews; Issue 4, No. CD004109 (no longer under consideration in light of Rule 132 Declarations of Drs. B. Muellinger and T. Hofmann).*

Jung, H., et al., "Treatment of Patients with uncontrolled Asthma using high dose inhaled Corticosteroids admistered by controlled Inhalation—A retrospective Analysis," Poster 1994 at the Annual Meeting of the European Respiratory Society in Vienna on Sep. 14, 2009, 12:50-2:40 p.m. in Hall A2.

Nelson, H. S., et al., "Fluticasone Propionate Powder: Oral Corticosteroid-Sparing Effect and Improved Lung Function and Quality of Life in Patients with Severe Chronic Asthma," J. Allergy Clin. Immunol., 103:2Pt 1:267-75, (Feb. 1999).

CN 201080006616.X Second Office Action, Mar. 22, 2013.

(Continued)

*Primary Examiner* — Jane C Oswecki

(74) *Attorney, Agent, or Firm* — Peters Verny, LLP

(57) ABSTRACT

Methods, devices and compositions for treatment of severe and uncontrolled asthma are provided by which high amounts of an inhaled corticosteroid are directed to the small airways of the lower lungs. The invention provides for a substantial decrease in the dose of concurrently administered oral corticosteroids. A particular advantage of the invention is the significant reduction in corticosteroid-related adverse effects.

22 Claims, No Drawings

(56) References Cited

OTHER PUBLICATIONS

Chen, G., et al., "Discussion on Efficacy of Oral Prednisone plus Inhalation Therapy in the Treatment of Children Suffering from Moderate and Severe Asthma," Department of Pediatrics, the No. 1 People's Hospital, Yancheng, Jiangsu Province 224000, Dec. 31, 2008.
MX/A/2011/008200 Office Action, May 7, 2013.
U.S. Appl. No. 13/605,451 non-final Office action, mailed Nov. 7, 2013.
Kohler, E., et al., "Lung Deposition after Electronically Breath-Controlled Inhalation and Manually Triggered Conventional Inhalation in Cystic Fibrosis Patients," J. of Aerosol Medicine, 2005, 18(4):386-395.
Adams, N., et al., "Inhaled Fluticasone Versus Inhaled Beclomethasone or Inhaled Budesonide for Chronic Asthma", Cochrane Database of Systematic Reviews, (2):CD002310 (2004). Update in Cochrane Database of Systematic Reviews, (1):CD002310 (2002).
Adams, N., et al., "The Dose-Response Characteristics of Inhaled Corticosteroids When Used to Treat Asthma: An Overview of Cochrane Systematic Reviews", Respiratory Medicine, vol. 100/Issue 8:1297-1306, (Aug. 2006).
Adams, N.P., et al., "Inhaled Fluticasone at Different Doses for Chronic Asthma in Adults and Children", Cochrane Database of Systematic Reviews, (3):CD003534 (Jul. 20, 2005): Update of Cochrane Database of Systematic Reviews. (1):CD003534 (2002).
Briese, M., et al., "Improvement of Alveolar Glutathione and Lung Function But Not Oxidative State in Cystic Fibrosis", Am. J. of Respiratory Critical Care Medicine, Jan. 15, 2004, V.169/15:822-828, XP009133675, Abst., p. 822, col. 2, Para. 5, p. 826, col. 1, Para. 4, p. 827, col. 2, Para. 2.
Dempsey, O.J., et al., "Relative Lung Delivery of Fluticasone Propionate via Large Volume Spacer of Nebuliser in Healthy Volunteers", Eur. J. Clin. Pharmacol., 57/9:637-41 (2001).
Global Initiative for Asthma, Global Strategy for Asthma Management and Prevention, pp. 59-61 (2008).
Hansel, T. T., et al., A Multinational, 12 week, "Randomized Study Comparing the Efficacy and Tolerability of Ciclesonide and Budesonide in Patients with Asthma", Clinical Therapeutics, Excerpta Medica, Princeton, NJ, Jun. 1, 2006, V28/6:906-920, XP025059785ISSN: 0149, retrieved on Jun. 1, 2006, p. 917, col. 2, Para 1.
Hayasaka, Naomi, et al., "Optimization of Dosing Schedule of Daily Inhalant Dexamethasone to Minimize Phase Shifting of Clock Gene Expression Rhythm in the Lungs of the Asthma Mouse Model", Endocrinology, Jul. 2007, V148/7:3316-3326, XP002582647 ISSN: 0013-7227 Abstract.
Karagiannidis, C., et al., "High-Altutude Climate Therapy Reduces Local Airway Inflammation and Modulates Lymphocyte Activation", Scand. J. Immunol., p. 304 (2006).
Mackenzie, CA, et al., "An Open Study to Assess the Long-Term Safety of Fluticasone Propionate in Asthmatic Children", International Study Group, Br.J.Clin. Pract., 48/1:15-8 (Jan.-Feb. 1994).
Nelson, H.S., et al., "Fluticasone Propionate Powder: Oral Corticosteriod-Sparing Effect and Improved Lung Function and Quality of Life in Patients With Severe Chronic Asthma", J. Allergy Clin. Immunol., 103:2Pt 1:267-75, (Feb. 1999).
PCT/EP2010/051321, International Search Report and Written Opinion, Jun. 8, 2010.
Pocket Guide for Asthma Management and Prevention, Global Initiative for Asthma, A Pocket Guide for Physicians and Nurses, pp. 1-28 (2008).
Powell, H., et al., "High Dose Versus Low Dose Inhaled Corticosteroid as Initial Starting Dose for Asthma in Adults and Children", Cochrane Database of Systematic Reviews, (2003), Issue 4, Art. No. CD004109. DOI: 10/10002/14651858. CD004109. pub. 2.
Scheuch, G., et al:, "Novel Approaches to Enhance Pulmonary Delivery of Proteins and Peptides", Journal of Physiology and Pharmacology, Polish Physiological Society, Krakaw, PL, Nov. 1, 2007, V58/ suppl. 5, No. 2, pp. 615-625, XP009128918, ISSN: 0867-5910, Abstract, p. 621, last paragraph.
Ververeli, K., et al., "Oral Corticosteroid-Sparing Effects of Inhaled Corticosteroids in the Treatment of Persistent and Acute Asthma", Annals of Allergy, Asthma and Immunology, 92/5:512-522(11), (May 2004).
Westbroek J., et al., "Oral Steroid-sparing Effect of Two Doses of Nebulized Fluticasone Propionate and Placebo in Patents With Severe Chronic Asthma", Resp. Med., 93/10:689-99, (Oct. 1999).

* cited by examiner

USE OF A GLUCOCORTICOID COMPOSITION FOR THE TREATMENT OF SEVERE AND UNCONTROLLED ASTHMA

CROSS-REFERENCE TO RELATED APPLICATIONS

This application is a Continuation-in-Part of the U.S. application Ser. No. 12/365,754, filed on Feb. 4, 2009, and a national stage of the PCT application PCT/EP2010/051321, filed on Feb. 3, 2010, that claims priority of the U.S. application Ser. No. 12/365,754, filed on Feb. 4, 2009.

BACKGROUND OF THE INVENTION

This invention concerns methods, devices and compositions for treatment of severe and uncontrollable asthma. It provides means for delivery of high doses of a suitable inhalable corticosteroid to the small and central airways of the lower lungs without need for simultaneous administration of oral corticosteroids or with a significantly decreased need for such simultaneous administration of oral corticosteroids. The method significantly increases delivery of the aerosolized inhalable corticosteroid into the bronchi, bronchioli, and alveoli of the central and lower peripheral lungs and decreases deposition of the corticosteroid into the bronchi and trachea of the upper lungs as well as in an oropharyngeal area and thereby significantly decreases or completely eliminates undesirable secondary (e.g. oropharyngeal) symptoms associated with delivery of high doses of inhalable corticosteroids. The method utilizes devices allowing individualization of treatment parameters in asthmatic patients having compromised breathing pattern due to severe and uncontrollable asthma.

Asthma is a major cause of chronic morbidity and mortality throughout the world and is one of the most prevalent chronic diseases, with estimated 300 million individuals affected by this condition.

People suffering from asthma may have either a mild form of asthma that is easily controlled with oral, systemic or inhalation therapy or a severe fowl of asthma that is difficult to control and treat. The severe fowl of asthma is connected with a heightened bronchial hyper-reactivity and with chronic severe and uncontrolled or poorly controlled asthmatic symptoms.

Many attempts have been made to control asthma with a particular emphasis on a control and treatment of patients suffering from the severe and uncontrollable asthmatic attacks. However, since each individual is unique in his/her degree of reactivity to environmental triggers, asthma affects each patient differently. This naturally influences the type, dose and a route of administration of various medication and treatments.

Global Initiative for Asthma (GINA) asthma guidelines have been established to determine the severity of asthma. Severe and uncontrollable asthma is classified by GINA guidelines as steps IV and step V, generally requiring administration of oral corticosteroids in combination with inhaled corticosteroids. For step IV, the preferred treatment is to combine medium to high doses of inhaled corticosteroid with a long-acting inhaled β-agonists. For step V, the above medication is further supplemented with orally administered glucocorticosteroids. Both treatments are known to cause or be associated with severe side effects, and these side effects may be exacerbated with a prolonged use of high-doses of inhaled corticosteroids.

As indicated already above, many attempts to successfully treat severe and uncontrollable asthma have been made. These attempts include development of new and more potent drugs, such as for example more potent corticosteroid fluticasone as well as new nebulizing technologies that affect pulmonary drug delivery.

Eur. J. Clin. Pharmacol, 57:637-41 (2001) describes a study comparing a large volume spacer and fluticasone nebulizer (FP-neb) in delivery of fluticasone propionate by inhalation in healthy volunteers. The large volume (750 ml) spacer was shown to produce about a sevenfold higher relative lung dose than nebulizer. This reference shows that the efficacy of the aerosol delivery depends on the device used for such delivery.

Respir. Med., 93(10):689-99 (1999) describes an oral steroid-sparing effect of high dose (4000 μg/day/bid) of inhaled fluticasone propionate. Reduction in orally administered prednisone was significantly greater in the group receiving 4000 μg of fluticasone propionate per day than 1000 μg per day. However, it is noticeable that using this technology, high percentage (37%) of all patients discontinued 4000 μg treatment, presumably for high occurrence of severe side effects.

J. Allergy Clin. Immunol., 103:267-75 (1999) describes an oral corticosteroids-sparing effect and improved lung function in patients with severe chronic asthma who received 500 or 1000 μg of fluticasone propionate administered twice daily. While this treatment eliminated a need for oral prednisone, topical adverse effects associated with inhaled corticosteroids were observed during this treatment.

Br. J. Clin. Pract., 48:15-8 (1994) assessed a long-term safety of fluticasone propionate in asthmatic children. Adverse effects were reported by 51% of patients even with such low doses as 50 or 100 μg administered twice a day via a dry powder inhaler.

Cochrane Database Syst. Rev., 2:CD002310 (2004) reviewed a potency of fluticasone propionate for treatment of chronic asthma and compared its effect to that of beclomethasone and budesonide. The study showed that fluticasone propionate, given at half the daily dose of beclomethasone or budesonide, resulted in improvement of forced expiratory volume in the first second (FEV1). Unfortunately, due to a larger deposition of the fluticasone in the upper lungs, it also had a higher risk of pharyngitis and other adverse side effects.

Cochrane Database Syst. Rev., 3:CD003534 (2005) describes use of inhaled fluticasone at different doses. While patients receiving 2000 g per day of fluticasone propionate were more likely to reduce a need for oral prednisolone then those on 1500 or 1000 μg/day, hoarseness and oral candidiasis were significantly greater for these higher doses.

Respiratory Medicine, 94: 1206-1214 (2000) investigated the efficacy and safety of nebulized fluticasone propionate compared to orally administered prednisolone. The nebulized fluticasone was at least as effective as oral prednisolone in the treatment of children with acute exacerbated asthma.

Cochrane Database Syst. Rev., 4:CD004109.pub2 (2008) evaluated the efficacy of an initial high dose of inhaled corticosteroids compared to a lower to moderate dose. Authors concluded that treatment should commence with a moderate rather than high dose of inhaled corticosteroids.

Annals Allergy, Asthma and Immunology, 92:512-522 (2004) reviewed the efficacy and safety of inhaled corticosteroids when used to reduce daily oral corticosteroid requirement in patients with severe asthma. Authors concluded that inhalable corticosteroid can reduce orally administered corticosteroids requirements in patients with persistent and exacerbated asthma. However, the question of increased adverse side effects still remains.

Respiratory Medicine, 93: 689-699 (1999) investigated the steroid-sparing effect of two doses of nebulized fluticasone propionate in patients with severe chronic asthma. The nebulized fluticasone at a daily dose between 1 and 4 mg was safe and effective means for reducing the oral steroids requirement of patients with chronic oral dependent asthma.

Disclosures discussed above indicate that a need for orally administered steroids in patients suffering from severe and uncontrollable asthma may be decreased by administration of appropriately high doses of inhalable corticosteroids. However, when such high doses of inhalable corticosteroid are administered, severe adverse side effects occur, preventing a truly efficacious treatment of these patients.

It would, therefore, be advantageous to have available a method and/or device and, or composition that provides for efficacious treatment for severe and uncontrollable forms of asthma, wherein a high dose of the inhalable corticosteroid is deposited at the site of asthmatic inflammation, namely in alveoli and bronchioli of the lower lungs combined with a low deposition of the corticosteroid in the trachea and in the oropharyngeal area, wherein orally administered steroids could be eliminated or, at least, the oral dose of these drugs could be significantly reduced.

It is, therefore, an object of this invention to provide a method, a device and/or a composition for efficacious treatment for severe and uncontrolled forms of asthma by providing means for delivery of a sufficiently high dosage of a corticosteroid for treatment of said severe uncontrolled asthma and wherein an oral delivery of corticosteroids could be either completely eliminated or reduced, and wherein said treatment would be able to deliver higher dosages of corticosteroid selectively into alveoli and bronchi of the lower peripheral lungs of an asthmatic patient without depositing said drug into a mouth or pharyngeal cavity or causing other undesirable adverse side effects.

A further object of the invention is to provide a device capable of delivering an inhalable glucocorticoid composition efficiently to the lower lungs while minimizing its deposition in other regions of the respiratory system.

A further object of the invention is to provide the combination of a device and an inhalable glucocorticoid composition which provides for the efficient delivery of a glucocorticoid to the lower lungs while minimizing its deposition in other regions of the respiratory system.

Further objects of the invention will become apparent on the basis of the description and patent claims.

SUMMARY OF THE INVENTION

In a first aspect, the invention provides an inhalable glucocorticoid composition for use in the therapy of a patient suffering from severe and uncontrolled asthma and an inhalation device by which the composition is administered as a nebulised aerosol. The device is adapted for emitting the nebulised aerosol during the inhalation phase of the patient at a rate of not more than about 20 liters per minute. Moreover, it is adapted for emitting, per inhalation phase, a total volume of at least 0.4 liters and preferably in the range from about 0.4 to about 2 liters of gas phase, said gas phase including the nebulised aerosol and optionally aerosol-free air. It is further adapted to emit, per inhalation phase, not more than about 150 milliliters of aerosol-free air before emitting nebulised aerosol. According to this first aspect, the invention further provides that the therapy includes the oral administration of a glucocorticoid at a daily dose which is not higher than about 40 milligrams of prednisolone or an equipotent dose, which daily dose is herein understood such as to include zero milligrams, i.e. no concurrent oral glucocorticoid therapy.

A further aspect of the current invention is a method for the treatment of severe and uncontrolled asthma by providing means for increasing efficacy of an inhalable corticosteroid delivery by delivering large dosages of such inhalable corticosteroid selectively to alveoli and bronchiole of the lower lungs of a patient without causing adverse side effects and secondary symptoms by incidental delivery of these corticosteroid to the oral cavity, throat and upper lungs.

Another aspect of the current invention is a method for treatment of severe uncontrollable asthma by providing means for delivering a larger percentage of dosages of a corticosteroid selectively to the lower lungs of a patient suffering from severe uncontrollable asthma and thereby eliminating or significantly reducing a need for concurrently administered corticosteroids orally or systemically.

Still another aspect of the current invention is a method for treatment of severe uncontrollable asthma with completely eliminated or with at least 30% reduced dose of orally delivered corticosteroid by providing means for treating such severe and uncontrollable asthma with a high dosage of a corticosteroid delivered as an aerosol having particle sizes predominantly from about 2 to about 6 μm, by nebulization using a nebulizing system that applies, during delivery into a patient's lungs, an overpressure enabling such delivery in less than 6-10 minutes and further resulting in selective delivery and homogeneous distribution of the corticosteroid in the lower lungs, wherein said nebulizing system is equipped to have a controlled airflow, and defined volume.

Yet another aspect of the current invention is a method for treatment of severe uncontrolled asthma with nebulized fluticasone, budesonide, beclomethasone dipropionate, budesonide, mometasone furoate, ciclesonide, flunisolide or triamcinolone acetonide wherein the clinical effect is reached without increasing systemic and local extrathoracic or oropharyngeal side effects.

Yet another aspect of the current invention is a method for treatment of severe uncontrolled asthma by inhalation of nebulized fluticasone as a representative corticosteroid administered into lungs via nebulizer with concentration of fluticasone in the nebulizer being higher than 200 μg ml, preferably 0.5-2 mg/mL, formulated as a suspension and with total filling dose of fluticasone not exceeding about 4000 μg, using a nebulizing system that applies overpressure during inhalation and thus assures selective deposition of more than 200 μg of said corticosteroid into the lower lungs in less than 6-10 minutes.

Yet another aspect of the current invention is a nebulizing system comprising a device able to provide an overpressure as well as a controlled air flow during a patient's inspiration time to reduce patient breathing effort with pressure at the nebulizer mouthpiece up to a positive pressure of between 0-40 mbar.

Another aspect of the current invention is a method for treatment of severe uncontrollable asthma by providing a nebulization protocol wherein, during one inspiration time and under the mean inspiratory flow rate equal to or below 20 l/min, the patient is subjected to a first volume of 150 ml or less of particle-free air in a predetermined time of less than 0.5 sec, followed by a second volume of between about 200 and about 3000 ml of an aerosol containing an inhalable corticosteroid administered in a predetermined time from about 1 to about 10 seconds, said aerosol preferably administered within less than 0.2 sec after the start of inspiration, followed by a third volume of between about 100 to about 500 ml of particle-free air, and wherein such protocol results in forcing said inhalable corticosteroid from the extrathoracic and tracheal airways to be deposited more selectively into the lower airways.

Yet another aspect of the current invention is a method for treatment of severe uncontrolled asthma by inhalation of nebulized corticosteroid in an aerosol having particle sizes predominantly in the range from about 2 to about 6 μm, preferably from about 3 to about 5 μm.

Another aspect of the current invention is a method for treatment of severe uncontrollable asthma by providing means for delivering larger dosages of a corticosteroid once a day selectively to the lower lungs of a patient thereby eliminate or significantly reduce a need for concurrently administered corticosteroid orally or systemically wherein asthma is improved without loss of FEV1 and with diminished adverse side effects.

Still another aspect of the current invention is a method for treatment of severe uncontrollable asthma by providing a nebulization system for individualization of the treatment wherein said nebulization system comprises a pre-programmable volume for drug delivery, a pre-programmable air flow delivery, a preprogrammable overpressure, and may further comprise a compliance monitoring system which allows the patient and the doctor to see and control frequency of the corticosteroid delivery, such means being any storage media, a smart card, a chip or a wireless communication connection that permits evaluation of the treatment during and after the end of a treatment period and determination of frequency of the corticosteroid administration.

Definitions

"Glucocorticoid" means a pharmaceutically acceptable glucocorticoid compound useful for oral and/or inhalable therapy. As used herein, such compound may also be referred to as "steroid" or "corticosteroid".

"Inhalable corticosteroid" means a corticosteroid that is suitable for delivery by inhalation. Exemplary inhalable corticosteroids are fluticasone, beclomethasone, budesonide, mometasone, ciclesonide, flunisolide, triamcinolone or any other corticosteroid currently available or becoming available in the future. The name of a glucocorticoid should be understood so as to include any pharmaceutically useful salts, solvates and physical foul's. For example, "fluticasone" is understood as including fluticasone propionate and fluticasone furoate. Other salts of interest include beclomethasone dipropionate, mometasone furoate, and triamcinolone acetonide.

"Oral steroid" means any corticosteroid that is suitable for oral or systemic treatment of asthma. Representative steroid are prednisone, prednisolone, methylprednisone, dexamethasone or hydrocortisone, including their pharmaceutically acceptable salts, solvates, and physical forms.

"Lower lungs", "small lungs" or "peripheral lungs" means an area of the lungs primarily containing bronchi, alveoli and bronchiole, a primary site of asthmatic inflammation, narrowing and constriction. Large and selective depositions of an inhalable corticosteroid in this area is eminently desirable and contributes to an efficacious treatment of severe uncontrolled asthma.

"Upper lungs", "central lungs" or "large lungs" means an upper area of lungs containing bronchi and trachea. Large depositions of an inhalable corticosteroid in this area are undesirable as they lead to adverse effects.

"Oropharyngeal area" or "extrathoracic area" means the oral cavity, nasal cavity, throat, pharynx and larynx. Any deposition of the inhalable corticosteroid in these areas is undesirable and leads to development of severe adverse effect such as hoarseness, loss of voice, laryngitis and candidiasis. It is preferable that there is no or a very little residual deposition, occurring primarily during expiration of the inhaled corticosteroid, in this region.

"One breath" means a period of time when a person inhales (inspires and exhales during a regular breathing pattern that includes inhaling and exhaling.

"Inspiration time" or "inspiration phase" or "inhalation phase" means the fraction of one breath when a person inhales.

"Expiration time" means a fraction of one breath when a person exhales the air, nitric oxide or another metabolite from the lungs. For the purposes of this invention, it is preferable that the aerosolized drug is forced with a slight overpressure into the lower lungs during inspiration and that it is not exhaled during expiration time or that only a small portion is exhaled.

"Bolus technique" means transportation of the corticosteroid aerosol to a predefined region in the lungs.

"FEV1" means forced expiratory volume in one second.

"VC" means vital capacity.

"ERV" means expiratory resting volume.

"Particle-free air" or "aerosol-free air" means air that does not contain any nebulised aerosol, or any drug. Such aerosol-free air may be delivered before and/or after the aerosolized drug.

"Overpressure inhalation" means inhalation with actively provided air that is preferably predefined in airflow for a predefined time. During inspiration the patient adjusts to the inspiratory flow rate. If the patient inhales more passively an overpressure of up to 40 mbar is applied during the inhalation phase to reduce the inspiratory effort. Consequently, the patient is able to inspire a more deep inhalation volume and inhale with a slower inspiration flow rate compared to a spontaneous inhalation.

"Severe and uncontrolled asthma" or "severe and uncontrollable asthma" means asthma which is, before or at the initiation of the therapy according to the invention, severe and/or uncontrolled and/or poorly controlled as classified according to the Guideline of the Global Initiative for Asthma (GINA), see e.g. Pocket Guide for Asthma Management and Prevention (updated 2009 by GINA). Practicing the invention will reduce the severity of the disease and achieve control of symptoms, therefore it is important not to apply the terms "severe" and "uncontrolled" or "uncontrollable" to the condition of a patient who has already undergone a therapy as claimed herein.

"Nebulised aerosol" means an aerosolized liquid. The liquid is dispersed in a gas phase which is frequently air. The dispersed liquid droplets have a particle size distribution which is suitable for inhalation therapy.

DETAILED DESCRIPTION OF THE INVENTION

In a first aspect, the invention provides an inhalable glucocorticoid composition for use in the therapy of a patient suffering from severe and uncontrolled asthma and an inhalation device by which the composition is administered as a nebulised aerosol. The device is adapted for emitting the nebulised aerosol during the inhalation phase of the patient at a rate of not more than about 20 liters per minute. Moreover, it is adapted for emitting, per inhalation phase, a total volume which is at least 0.4 liters, and preferably in the range from about 0.4 to about 2 liters liters of gas phase, said gas phase including the nebulised aerosol and optionally aerosol-free air. It is further adapted to emit, per inhalation phase, not more than about 150 milliliters of aerosol-free air before emitting nebulised aerosol. According to this first aspect, the invention further provides that the therapy includes the oral administration of a glucocorticoid at a daily dose which is preferably not higher than about 40 milligrams of prednisolone or an equipotent dose, which daily dose is herein understood such as to include zero milligrams, i.e. no concurrent oral glucocorticoid therapy.

The inhalable glucocorticoid composition comprises a pharmaceutically acceptable glucocorticoid in a liquid formulation suitable for being delivered as a nebulised aerosol. Several compositions which are appropriate for this purpose are known and available for therapy. These compositions are typically aqueous solutions or suspensions comprising a glucocorticoid compound such as fluticasone propionate, budesonide, beclomethasone dipropionate, ciclesonide, flunisolide, mometasone furoate, or triamcinolone acetonide. The strength of the compositions depends on the active ingredient. Examples for suitable strengths include 0.25/ml or 1 mg/ml fluticasone propionate, 0.4 mg/ml for beclomethasone dipropionate, and 0.25 mg/ml or 0.5 mg/ml for budesonide. However, higher or lower strengths may also be useful.

The dose of the glucocorticoid to be filled into the inhalation device should normally be in the range from about 400 micrograms to about 4,000 micrograms. However, depending on the severity of the condition, the status of the patient and the selected glucocorticosteroid, the dose may also be higher or lower than this range. The dose may also be selected within the ranges typically referred to as “medium daily dose” or “high daily dose”, taking the number of dosings per day into consideration.

The inhalable composition and the inhalation device according to the invention are to be used for the treatment of patients who, before the claimed therapy is conducted, suffer from severe and uncontrolled asthma. For these patients, the concurrent therapy with an orally administered glucocorticoid is typically indicated. Within this context, concurrent therapy means the administration of an oral glucocorticoid composition on at least days during the course of the therapy. For the avoidance of doubt, concurrent therapy does not require that the oral co-medication is administered at the same time when the inhalable composition is administered.

The orally administered glucocorticoid, if any, may for example be selected from the group of hydrocortisone, dexamethasone, prednisone, prednisolone, and methylprednisolone. This glucocorticoid may be given once a day or divided into several doses per day. The daily dose of the orally administered glucocorticoid is only low or moderate. According to the invention, the dose is not more than about 40 milligrams of prednisolone, or an equipotent dose of another glucocorticoid. For the avoidance of doubt, the dose may and will often be higher before and at initiation of a course of therapy according to the present invention. During the therapy as defined in claim 1, however, the dose of the orally administered glucocorticoid is reduced to not more than about 40 milligrams of prednisolone per day, or an equipotent dose of another glucocorticoid. Preferably, the daily dose is reduced to not more than about 30 mg or not more than about 25 mg of prednisolone per day, or not more than about 20 mg of prednisolone per day, such as about 0 to 20 mg per day, or an equipotent dose range if another glucocorticoid is used.

In a further preferred embodiment, the initial daily dose of the orally administered glucocorticoid is reduced during the course of therapy by at least about 20%, and more preferably by at least about 30%. In a further embodiment, the dose is decreased to zero, either gradually during the course of therapy, or immediately as the patient is switched from conventional therapy to the therapy of the invention. The great benefit of a reduced oral glucocorticoid dose lies in a substantial reduction of adverse effects as associated with systemic glucocorticoids, such as immunosuppression, hyperglycemia, increased skin fragility, negative calcium balance due to reduced intestinal calcium absorption, osteoporosis and reduced bone density, weight gain due to increased visceral and truncal fat deposition, adrenal insufficiency, proteolysis etc.

Equipotent doses of other orally administered glucocorticoids may be easily calculated based on e.g. Knoben J E, Anderson P O., Handbook of Clinical Drug Data, 6th ed. According to this source, as well as other handbooks, the following doses of glucocorticoids are approximately equipotent with respect to their glucocorticoid effects: Cortisone 100 mg; hydrocortisone 80 mg; prednisone 20 mg; prednisolone 20 mg; methylprednisolone 16 mg; dexamethasone 2 mg.

The inhalation device is adapted to emit, or deliver to the patient via a mouthpiece, the nebulised aerosol at a low flow rate (or output rate). Such low inspirational flow rate is advantageous as it reduces the fraction of aerosol droplets which are deposited in the upper airways, thus increasing the fraction of aerosol which is actually delivered to the deep lungs. According to the invention, the flow rate is restricted to not more than about 20 liters per minute. More preferably, the flow rate is not more than about 300 milliliters per second, or not more than about 250 milliliters per second, such as about 200 milliliters per second. This is in contrast to conventional breathing patterns by which patients often inhale nebulised aerosols at inspirational flow rates of 500 milliliters per second or more. Preferably, the device emits the aerosol only during the inhalation phase.

The inhalation device may also be adapted to emit aerosol-free air during the inhalation phase. This air may be emitted before and/or after the nebulised aerosol. However, according to the invention, the volume of aerosol-free air emitted before the aerosol is delivered must be kept relatively low. It should not be higher than about 150 milliliters. In a further embodiment, the volume of aerosol-free air emitted before the aerosol not more than 100 milliliters. The beneficial effect of this restriction is that the medicated aerosol which is delivered early during the inhalation phase has a higher chance for reaching the deep lungs.

The total volume of gas phase emitted by the inhalation device adapted according to the invention is considerably higher than the volume which patients would normally inhale intuitively. The total volume is at least about 0.4 liters, and preferably in the range from about 0.4 to about 2 liters, in particular from about 0.4 to about 1.4 liters. For patients having very large lung volumes, higher total gas phase volumes may also be used.

Preferably, the total volume of emitted gas phase is selected individually per patient on the basis of the patient’s functional lung parameters as determined prior to or at the time of initiating the therapy of the invention. For example, the selected total volume may be based on the patient’s inhalation (or inspiratory) capacity (IC). In a preferred embodiment, the total volume is at least about 40% of the patient’s inhalation capacity. More preferably, it is in the range from about 40% to about 110% of the patient’s inhalation capacity, in particular from about 40% to about 70% for patients having an inhalation capacity of at least about 1.2 liters and from about 50% to about 110% for patients having an inhalation capacity of less than about 1.2 liters. For a patient with an inhalation capacity of about 0.6 liters or less, the total volume is preferably selected to be at least about 65% of the inhalation capacity, such as about 70% to about 110%.

The total volume of emitted gas phase per inhalation phase may also be selected on the basis of the forced expiratory volume exhaled in one second (FEV1) and its deviation from the predicted FEV1 value, using appropriated normal values for the person's gender, age and height. The smaller the actual FEV1 compared to the predicted FEV1, the greater is the severity of the asthma. For example, for a patient exhibiting an FEV1 which is at least about 80% of the predicted FEV1, the total volume of emitted gas phase should preferably be selected in the range from about 45% to about 75% of the actual FEV1, in particular from about 50% to about 70%. On the other hand, for a patient whose actual FEV1 value is about 50% to about 80% of the predicted FEV1, the total volume of emitted gas phase should preferably be selected in the range from about 50% to about 90%, in particular from about 55% to about 85% of the actual FEV1. If the patient's actual FEV1 value is from about 30% to about 50% of the predicted FEV1, the total volume of emitted gas phase should preferably be selected in the range from about 65% to about 110%, and particularly from about 70% to about 105% of the actual FEV1 value. If the patient is severely affected and his FEV1 is less than about 30% of the predicted FEV1 value, the total volume of emitted gas phase should preferably be selected in the range from about 75% to about 170%, and in particular from about 80% to about 160%, or from about 120 to about 160% of the actual FEV1.

As mentioned, the inhalation device may be configured to emit not only the nebulised aerosol, but also aerosol-free air. In a specific embodiment, the inhalation phase may be divided into three consecutive phases: a first phase in which the inhalation device emits a small amount of aerosol-free air; a second phase in which the device delivers the nebulised aerosol; and a third phase in which again a volume of aerosol-free air is emitted. The volume of the aerosol-free air emitted in this third phase may be, for example, in the range of 200 to 500 milliliters.

The volume of the nebulised aerosol itself which is delivered by the device may be selected taking into account the specific glucocorticoid, the strength of the composition, and the patient. In one of the preferred embodiments, this volume is in the range from about 200 to about 3,000 milliliters.

The inhalation device is further adapted to deliver an aerosol having an optimal particle size distribution for homogenous deposition in the lower lungs to prevent high losses of drug in the oropharynx as well as losses in the upper airways. The invention therefore provides for an aerosol having sizes of aerosolized particles corresponding substantially to a size of the alveoli and bronchiole. A suitable particle size for targeting the alveoli and bronchiole is between 2 and 6 micrometers. Particles larger than that are selectively deposited in the upper lungs, namely bronchi and trachea and in the mouth and throat, i.e. oropharyngeal area. Accordingly, the inhalation device is adapted to produce an aerosol having a mass median aerodynamic diameter (MMAD) in the range from about 2 to about 6 micrometers, and preferably in the range from about 3 to about 5 micrometers. In a further embodiment, the particle size distribution is narrow and has a geometric standard deviation (GSD) of less than about 2.5.

According to a further preferred embodiment, the device is adapted such as to emit the nebulised aerosol during the inhalation phase of the patient at an overpressure of up to about 40 mbar. Moreover, it is preferred that the patient performs the inhalation in such a way that an overpressure (or positive pressure) of the aerosol is maintained. Preferably, the overpressure is at least about 1 mbar. In further embodiments, the overpressure is at least about 2 mbar, 3 mbar, and 5 mbar, respectively. Such overpressure is typically achieved with a compressor or pump unit attached to the nebulizing device where such unit is optionally further equipped with a timer so that the overpressure period is limited strictly to a fraction of the inspiration time when the corticosteroid is delivered. In another embodiment, the overpressure is initiated by a patient's inspiration time breathing. When the patient inspires with overpressure, the patient's breathing effort is reduced. Consequently, patients with severe asthma are able to perform a deeper and slower breathing pattern, compared to spontaneous inhalation without overpressure.

During inhalation, the device is adapted to provide a slight overpressure to the aerosol to allow preferable deposition of the aerosolized drug into the deep lung and prevent its removal during expiration. During expiration, the overpressure is not applied and the patient exhales normally, without any airflow or pressure being applied.

In a further embodiment, the inhalation device is adapted to emit gas phase—including the nebulised aerosol—only after breath actuation by the patient. Breath actuation may by achieved by incorporating a pressure sensor into the device which is capable of detecting the slight underpressure which is caused when a patient initiates the inhalation phase by contracting the diaphragm, which results in the expansion of the intrapleural space causing an increase in negative pressure.

As mentioned, the current invention also relates to a method for treatment of severe and uncontrollable asthma by providing a means for delivery of high doses of a suitable inhalable corticosteroid directly to the small airways of the lower lungs without need for simultaneous administration of oral corticosteroids or with decreased need for such simultaneous administration of oral corticosteroids. The method significantly increases delivery of the aerosolized corticosteroid into the alveoli and bronchioles of the lower peripheral lungs and decreases deposition of the corticosteroid into the bronchi and trachea of the upper lungs as well as in an oropharyngeal area and thereby significantly decreases or completely eliminates undesirable secondary symptoms. The method utilizes devices allowing individualization of a delivered volumetric flow and vaporized aerosol together with a controlled airflow and with airflow overpressure conditions in asthmatic patients with compromised breathing pattern.

Asthma is a chronic inflammation of the bronchial tubes of airways that causes swelling, bronchial narrowing and constriction. As a consequence, patients suffering from asthma have difficulty breathing. The bronchial swelling, narrowing and constriction is generally treated with oral or inhalable drugs, preferably with inhalable steroids, such as fluticasone, budesonide, beclomethasone, mometasone, ciclesonide, flunisolide, triamcinolone acetonide and any other corticosteroid suitable for inhalation therapy.

A mild form of asthma may be easily controlled and treated with a great variety of oral, systemic or inhalation therapies. Severe forms of asthma are characterized with a heightened bronchial hyper-reactivity and with other chronic symptoms. Treatments for the individuals suffering from the severe uncontrollable asthma are very difficult and complex.

The currently available treatments for asthma are largely dependent on the severity of the disease. In most cases, these treatments involve administration of steroids, whether orally administered corticosteroids (OCS), such as prednisone or prednisolone, or inhalable corticosteroids (ICS), such as fluticasone, beclomethasone, budesonide, mometasone, ciclesonide, flunisolide or triamcinolone acetonide in a therapeutic dose. These treatments may be, in some cases, supplemented with other drugs, such as, for example, bronchodilators as β-agonists. Since the orally or otherwise systemically delivered corticosteroids cause rather severe side effects and secondary symptoms in the patients and their systemic delivery affects the whole body, the corticosteroids locally administered by inhalation are highly preferred as a current treatment for asthma.

The moderate and more severe asthma patients, including the pediatric and geriatric asthma population, are frequently treated with nebulized inhalable corticosteroids using jet or ultrasonic nebulizers. These nebulizers typically deliver a filling volume of 1 or 2 ml of liquid solutions or suspensions containing about 200 micrograms of inhalable corticosteroids and maximum up to 2000 micrograms. Inhalable corticosteroids are also delivered by metered dose inhalers (MDI) and dry powder inhalers (DPI), at nominal doses at around 100 micrograms. These doses are mostly sufficient for treatment of mild forms of asthma where the quantity of the delivered dose is not critical for ameliorating asthmatic symptoms.

For severe asthmatic forms, however, the quantity of the dose delivered to the site of the asthmatic inflammation is often critical and decisive of the successful treatment. The currently recommended nominal doses for efficacious treatment of severe asthma range between 400 and 1600 μg. The amounts deposited at a site of inflammation, in alveoli and bronchioles of the lower lungs, are in the order of 10-25%, but mostly in the order of 10-15% of the above nominal dose, resulting in a maximum deposited lung dose of 250 micrograms. It would be an advantage to deliver and deposit between 400 and 800 micrograms in the lungs and mostly in the lung periphery.

Unfortunately, due to their inefficiency, none of the currently available nebulizing system is able to deliver such a dose into the lower lungs without causing serious adverse reactions. In the case of suspension formulations, the currently available nebulizers typically deliver only about 5% and up to maximum of 10% of the total dose of the corticosteroid placed in the nebulizer. Since corticosteroid suspensions are difficult to nebulize, much of the drug remains in the nebulizer. Therefore, the efficiency of nebulizers for delivering corticosteroid suspensions is much lower compared to inhalation solutions. Additionally, many other disadvantages are observed with currently available treatments, particularly as those treatments concern a treatment of severe and uncontrollable asthma.

Primary disadvantages of the currently available treatments with steroids are connected with the pharmacological effects of steroids, particularly when delivered orally or systemically and not directly to a targeted organ needing such treatment. Such oral or other systemic administration of steroids affects the whole body with targeted organ receiving only small amounts of the administered drug. This, of course, results in a need for administration of large doses of the steroids. Because of the overall pharmacological effect of orally and systemically delivered steroids, a targeted topical administration would seem to be a more preferred route of steroid administration. However, such targeted topical delivery of steroids by inhalation is also not without problems.

The currently used nebulizers typically deliver only a fraction of a total dose placed into the nebulizer. Thus, for example, from a total dose of 2000 micrograms placed into the nebulizer before aerosolization, only about 5-10% of the total dose may actually be deposited at a site of the asthmatic inflammation in the alveoli and bronchiole of the lower lungs and therefore the actual deposited dose at such site is only about 100 to 200 micrograms. This dose may be insufficient to treat severe asthma. The remaining 90-95%, that is 1800-1900 micrograms, of the drug is either deposited in the upper lungs, or in the oropharyngeal area (causing oropharyngeal side effects, such as *candida* infection or hoarseness), or it is exhaled or it remains in the nebulizer and is wasted. The amount of drug deposited in other sites of the respiratory system than the deep lungs may lead to undesired effects such as hoarseness, alteration of voice, laryngitis, candidiasis and irritation of the upper lungs and oropharyngeal area.

Normally, the inhaled steroid dose filled into the device cannot be simply increased above 2000 micrograms when using conventional nebulizers, because of the severe side effects such as candidiasis, soreness, hoarseness, laryngitis or voice alteration, which are sometimes observed even after low or moderate doses of inhalable corticosteroids. Again, the reason for this is the high mouth and throat deposition of the corticosteroid with the currently used inhalation systems.

A further disadvantage of the currently available treatment lies in many patients' lack of compliance with a proper nebulizer use. The inhalation devices which are currently used and available will often deposit only up to 200 micrograms in the deep lungs, but only when the patients inhale appropriately. It is well known that only a few of the patients use an inhalation device correctly. Commonly observed mistakes by the patients during an inhalation maneuver are: breathing is too fast, breathing is too shallow or the breathing is not coordinated. When the patient breathes too fast, inhalation flow rate results in extremely high drug deposition in the back of the throat and the larynx, with almost no drug deposition in the deep lungs. When the patient's breathing is too shallow, a shallow breath takes on only a small inhalation volume that cannot transport the aerosolized drug particles deep into the lungs thereby resulting in minimal deep lung deposition. When the breathing is not well coordinated, for example when the aerosol production and the inspiration phase of a patient are not in line, much of the emitted aerosol is not even inhaled. Moreover, some patients only take the drug when asthmatic symptoms occur and not continuously in a controllable manner. Patients with a poor breathing maneuver rarely profit from the inhalation therapy, because they generally do not get a sufficient amounts of the drug into the lungs. Since these patients also have more side effects caused by the high extrathoracic deposition, an abortion of and withdrawal from inhaled corticosteroid therapy is more likely. Such patients may be required to take oral steroids and, accordingly, become adversely affected by the known side effects of systemic corticosteroids.

The method for treatment of asthma, particularly severe and uncontrollable asthma according to the current invention provides several advantages over the currently available treatments. In a first aspect, the method allows the deposition of high doses of inhalable corticosteroids in the lower lungs of patients, without increasing corticosteroid deposition in the mouth, throat and lower lungs and provides for the drug aerosolized particles to be deposited deep into the lungs during breathing. The method provides an aerosol having the optimal particle sizes for homogenous deposition of the drug in the lower lungs that prevents high losses of drug in the oropharynx. During the inhalation, the nebulizer provides a slight overpressure during delivery of the aerosol to allow preferable deposition of the aerosolized drug into the deep lung and prevent exhalation of aerosol during the exhalation phase.

In a specific embodiment, the method defines a partition of one breath into two fractions, namely an inspiration time and expiration time wherein during the inspiration time a so called bolus technique is used to transport the drug containing aerosol to a predefined region in the lungs and, during the expiration time, to exhale a minimum of the drug from the lungs at end of the breath. The method of the invention results in a high deposition of between 400 and 1000 micrograms of the total 2000-4000 micrograms of corticosteroid drug filled in the nebulizer into the lower lungs of the patient in less than 6 to 10 minutes, in average, and permits decreasing or eliminating the need for a concurrent administration of orally administered steroid.

The method enables the deposition of a 2-4 times higher percentage of the total drug placed in the nebulizer in the lower lungs than previously possible. When the conventional methods achieved deposition of only about 200 micrograms of the corticosteroid in the patient's lung from the total dose of 2000 micrograms supplied to the nebulizer, the current method achieves between 400 and 1000 microgram deposition, preferentially in the lower lungs. Moreover, such dose is sufficient for replacing a twice daily dosing with 2000 mg of the corticosteroid with once daily dose of the 2000 micrograms, or with a twice daily dose of 1000-2000 micrograms to achieve amelioration of severe asthmatic symptoms. Additionally, the amount of the corticosteroid in the lower lungs is significantly larger compared to the amount of corticosteroid deposited in the upper lungs and particularly in oropharyngeal area.

The method allows deposition of the larger amount of the corticosteroid in the lungs without many undesirable adverse effects previously observed with administration of lower amounts of the drug in the lower peripheral lungs. The previously observed side effects, such as hoarseness, soreness, loss of voice, laryngitis or candidiasis due to the deposition of large amounts of the corticosteroid in the mouth and throat are suppressed or not observed with the current method.

In a further embodiment, the method defines a partition of one breath into two fractions, namely an inspiration time and expiration time wherein during the inspiration time a bolus technique is used to transport the drug containing aerosol to a predefined region in the lungs and, during the expiration time, to expire a minimum of the drug from the upper lungs and from oropharyngeal area. In a further embodiment, the inspiration time may be further divided into subfractions where the particle-free air is delivered both before and after the aerosol.

Per drug amount deposited in the lungs, the method provides for shorter delivery or administration times than conventional nebulizers. Typically, the delivery of the 200 micrograms of the corticosteroid would take between 5 to 20 minutes using a conventional jet nebulizer. The current method provides for a deposition of more than 400 micrograms in the lungs in less than 10 minutes, preferably in less than 6 minutes.

The method of the invention permits weaning of the asthmatic patient from the oral corticosteroids. With improved local delivery of the drug to the lower lungs in 2-4 times higher doses achieved with once daily administration, the patients are able to withdraw from oral corticosteroids treatment within a period of about two to about five weeks, during which time the oral dose of the corticosteroids is slowly decreased. Moreover, such withdrawal is possible without decrease in FEV1 and in some instances with actual increase of the FEV1 and without significant adverse reactions. This is particularly true when the used corticosteroid is fluticasone administered at a daily dose of 2000 micrograms. Typically, the degree and onset of asthma improvement is observed within 2-5 weeks of therapy. Such improvement may occur without necessity of oral corticosteroid and often results also in improved pulmonary functions such as increased FEV1 and with decreased inflammation.

The protocol for a therapy of severe asthma according to the invention may, for example, include several steps. First, the patient may be evaluated to determine the severity of the asthma under Global Initiative for Asthma (GINA) guidelines. Asthmatics with severe and uncontrolled asthma are classified as step IV or step V, described as a serious chronic condition often with exacerbation. Oral corticoid dose (OCS), asthma control, exacacerbations, FEV1, exhaled nitric oxide, vital capacity and other pulmonary functions are measured and recorded.

Subsequently, a mode and regimen of the treatment may be determined. Such mode may involve an initial combination of the inhalable and oral treatment with corticosteroids and optionally in combination with bronchodilators as β2-agonists or other drugs, as appropriate. For example, the patient may be treated with up to 150 mg of prednisone or prednisolone per day. The regimen for the treatment involves determination of an appropriate inhalable corticosteroid, appropriate daily dose and appropriate daily delivery once, twice or in rare circumstances, three times per day. For patient's convenience and practicality, once daily (QD) delivery is most preferable and may result in better compliance than an administration twice a day (BI)) or three times per day (TID).

Once the mode and regimen of the treatment is determined, an appropriate inhalation device capable of carrying out the invention and an appropriate inhalation procedure is selected.

A patient may then be treated once daily, in some instances twice daily, with more than 200 up to 4000 micrograms of an inhalable corticosteroid, depending on the selected inhalable corticosteroid. The inhalable corticosteroid may be selected from the group consisting of fluticasone, flunisolide, beclomethasone dipropionate, budesonide, mometasone furoate, ciclesonide and triamcinolone acetonide. In one of the preferred embodiments, 2000 microgram of fluticasone propionate are administered once or twice per day using an inhalation device capable of, and adapted to, emitting an aerosol in the manner specified in the patent claims. A useful device which is capable of being adapted such as to carry out the invention is the AKITA inhalation system which can control the breathing pattern of a patient during administration. Depending on their specific configuration, other inhalation systems capable of generating a nebulised aerosol, in particular breath-activated nebulisers, may also be used.

While the exact efficacious dose for treatment of severe asthma for each inhalable corticosteroid may not be known, it is likely that the effective deposited dose for severe asthma is >400 micrograms, and even more likely in the range of about 600-1000 micrograms. In a specific embodiment, the concurrent treatment with oral corticosteroids is continued but is gradually decreased to doses lowered by at least 30% of the initial oral dose or eliminated altogether. Typically, such decrease occurs within 2-3 weeks. Complete elimination of the steroid may happen in 3-5 weeks, but it may also take longer.

Treatment may continue daily and the patient may be periodically evaluated for pulmonary functions including FEV1. Every time the patient's pulmonary functions are stabilized with an initial oral dose of the steroid, the oral dose of the steroid may be lowered and maintained until patient's pulmonary functions are again stabilized. This process may continue until the patient is weaned from the oral corticosteroid completely or until the patient is stabilized at certain low level of oral corticosteroid. Typically, the oral dose of the steroid is decreased by at least 20%, and often by at least 30% of the initial dose. If appropriate in view of the progress of the patient, it is preferably completely eliminated.

The selected corticosteroid in the predetermined amount is placed into the inhalation device, such as the nebuliser component of the AKITA system. For example, 2000 micrograms of fluticasone may be loaded in form of an aqueous suspension or solution whose volume is typically in the range of 1 to 5 ml. Fluticasone is typically available as a suspension, and exhibits a steroid concentration of about 1 mg/mL. In the case other AKITA system, the nebulizer is directly connected with the mouthpiece that is further equipped with a pressure sensor and connected with a compressor. Inhalation period (inspiration time) may be preset to a pattern comfortable for a patient, for example, from 1 to about 10, preferably about 3-4 seconds of inspiration time.

When the patient inhales from the mouthpiece, the pressure sensor responds and starts inhalation by providing a positive overpressure or opening of an inspiration valve. The nebulizer or aerosol system is supplied with compressed air overpressure of up to 40 mbar and the corticosteroid is aerosolized and discharged as a corticosteroid containing aerosol at a preselected flow rate and with preselected overpressure. The overpressure lasts for the entire inspiration time. When the inspiration time is preselected, the overpressure is automatically stopped or shut off because the compressed air supply is interrupted at the end of the inspiration time. After a period allocated for exhaling, the process is repeated on and off for the entire period of inhalation, preferably for less than 6 minutes. During the inhalation time, the whole dose is preferably aerosolized with some residue remaining in the nebulizer. The nebulizer can be a liquid or dry powder aerosol system.

When this method of delivery is selected, during the inspiration time the aerosolized corticosteroid is forced under the overpressure into the lower lungs. When the overpressure is withdrawn and the patient exhales, the drug forced into the lower lungs is not easily displaced and remains there resulting in substantially higher deposition of the drug in the peripheral lungs than would happen with a normal breathing without overpressure. During the exhalation time, the small amount of the drug but is exhaled is the one that was in the upper lungs at the last moment of the inspiration time. Some fraction of this small amount may be deposited in the upper lungs or oropharyngeal area but most of the drug is exhaled to the outside of the mouth.

When the above treatment was performed on more then one hundred patients with inhalable fluticasone (2000 μg), administered once a day for 22 days, as described in Example 1, such treatment resulted in significant improvement of FEV1 by approximately 17% with simultaneous reduction in oral corticosteroid use by approximately 33%. Additionally, pulmonary inflammation, measured by exhaled nitric oxide, was reduced by approximately 44.5%.

In a preferred embodiment, a method for treatment of a patient suffering severe and uncontrollable asthma and requiring a concurrent treatment with oral corticosteroids comprises administering to an asthmatic patient an inhalable treatment comprising administration of an inhalable corticosteroid selected from the group consisting of fluticasone, beclomethasone dipropionate, budesonide, mometasone furoate, ciclesonide, flunisolide and triamcinolone acetonide and delivered as an aerosol containing the selected corticosteroid in amount from about 400 to about 4000 micrograms, where the aerosol is generated by a nebulizer device able to administer an aerosolized corticosteroid into lower lungs with a slight overpressure of maximum of 40 mbar or less, wherein such overpressure forces the aerosol into the lower lungs and results in deposition of more than 200 micrograms deposition of the corticosteroid into the lower lungs. This treatment further results in reduction of a need for concurrent treatment with oral steroid by at least 30%, in improvement of pulmonary functions and in reduction or elimination of oropharyngeal side effects.

In another embodiment, a selected corticosteroid is fluticasone administered in amount of about 4000 micrograms resulting in deposition of more then 200 micrograms in the lower lungs and preferably in the lung deposition larger than 400 micrograms. In another embodiment, the requirement for concurrent treatment with oral steroids is completely eliminated in about 2 to 5 weeks and such treatment results in improvement of asthma symptoms, in increase of the FEV1 evidencing an improvement of pulmonary functions and in reduction of lung inflammation.

Another embodiment involves use of a nebulizing system that is actuated by patient's breathing and the breath actuated nebulizer is used or an inhalation system for control of breathing pattern, known as AKITA inhalation system and device. In another embodiment, the method provides for inhalation treatment administered once, twice or three times a day, preferably only once a day with all benefits for asthma improvement. In another embodiment, the method shortens time for delivery and the inhalation treatment is accomplished in less than 6 and maximum up to 10 minutes.

In another embodiment, the aerosol is provided that has a particle sizes primarily within a range of alveoli, bronchiole or bronchi with aerosol having particle sizes from about 2 to about 6 microns MMAD, preferably particle size from about 3 to about 5 microns MMAD.

Using a nebulizer system such as the AKITA device, the selected corticosteroid in the predetermined amount and volume is placed into the drug cartridge connected with a nebulizing device that also includes the mouthpiece and a spirometer. The predefined volume of aerosolized particles is delivered into the flow path through which the patient is inhaling. Inhalation time is preset to comprise a three predefined periods. The first predefined time period is for delivery of aerosol particle-free air into the lungs at a flow rate that is also preset. The second predefined period is for delivery of a predefined volume of aerosolized particles of the corticosteroid, also at a preset flow rate. The third predefined period is for delivery of the second predefined time period of particle-free air. Optionally, the first time period can also be set to zero seconds, meaning that the aerosolization will start immediately. During the inhalation, patient is instructed to begin inhalation and during each inspiration time, the three (or two) predetermined periods are repeated. At the end of the second particle free period, that is after the third predefined period, a patient is instructed to stop inhaling and exhale. The reason for the second predefined time period of aerosol particle free air delivery into the lungs at a flow rate within the preset flow rate range is to move the aerosolized particles out of the upper airway region. In that way the upper airway region (mouth, throat, oropharynx, larynx and trachea) is emptied from remaining aerosol particles and the deposition of the drug in this region is reduced.

The method may also comprise a step of detecting when the subject is inhaling through the flow path and may further comprise steps of measuring and adapting the first, the second and the third predefined time period and/or the predefined volume of aerosolized particles to patient's health parameters.

The method may involve a step of determining optimal time intervals for administration of the first particle-free air, for administration of an aerosolized inhalable corticosteroid and for administration of the second particle-free air, wherein the cumulative time for these three time intervals correspond to one inspiration time. The time for each of the interval corresponds to from about 1 millisecond to about 10 sec, preferably from about 200 millisecond to about 5 seconds and may be the same or different for each interval. The flow rate is a predetermined fixed flow rate, wherein the first predefined particle-free air volume is up to about 0.15 liters, the predefined volume of aerosolized particles is up to about 3 liters and the second predefined particle-free air volume is up to about 0.5 liters. The nebulizer used for this method should be equipped to detect when the subject is inhaling through the flow path and prevent flow through the flow path after providing the second predefined time period of aerosol particle-free air.

In a further embodiment, the invention concerns a method for treatment of a patient having severe and uncontrollable asthma requiring a concurrent treatment with oral corticosteroids and comprises a treatment protocol where a patient is treated with an aerosol comprising an inhalable corticosteroid selected from the group consisting of fluticasone, fluticasone propionate, beclomethasone dipropionate, budesonide, mometasone furoate, ciclesonide, flunisolide and triamcinolone acetonide in amount from about 400 to about 4000 micrograms. The treatment protocol is set on one inspiration time divided into three predefined periods when the aerosol is administered in the second period. The three periods last from about 1 millisecond to about 10 seconds, preferably the first period lasts from 1 millisecond to about 1 second, the second period lasts from about 0.1 to about 10 seconds and the third period lasts from about 0.1 to about 5 seconds. An aerosolized particle-free air is administered at a preset flow rate and a preset volume during the first period, followed by a second period when an aerosolized corticosteroid is administered at a preset flow rate and a preset volume and is followed by a third period when, again, an aerosolized particle-free air is administered at a preset flow rate and a preset volume to clean the extrathoracic and tracheal airways of the corticosteroid and to force it deeper into the lungs. After the third period, the patient is instructed to stop inhaling and exhale. This protocol is repeated for about 6 to about 10 minutes or less, typically until a sufficient amount of the corticosteroid, that is larger than 200 micrograms, is nebulized and delivered into the lower lungs.

In a further embodiment, the preset inspirational flow rate and is equal to or lower than 20 liters/minute. In yet another embodiment, the preset flow rate is from about 3 to about 6 liters per minute and the aerosolized particle-free air administered in the first period is administered at a preset volume of less then 150 ml in about a half a second time, the corticosteroid aerosol administered in the second period is administered at a volume of from about 200 to about 3000 ml or in a preset time of from 1 to about 10 seconds and the aerosolized particle-free air administered in the third period is administered at a preset volume from about 200 to about 500 ml in about 0.3 to about 3.5 seconds time.

In another embodiment, the method involves a reduction of oral corticosteroids requirement by at least 30% or in a complete elimination for an orally administered corticosteroid, still resulting in improvement of asthma symptoms, in improvement of pulmonary functions determined by the FEV1 increase, in reduction of a lung inflammation and in overall reduction of oropharyngeal side effects.

In another embodiment, the selected corticosteroid is fluticasone administered in amount of about 200 micrograms once a day resulting in the lower lung deposition of fluticasone larger than 400 micrograms. In another embodiment, the aerosol administered during the inspiration time and comprising three predefined periods is generated by breath actuated nebulizer. In another embodiment the treatment protocol as outlined above is repeated once, twice or three times a day, the treatment is accomplished in less than 6 to 10 minutes. In another embodiment, the aerosol has predetermined size of particles from about 2 to about 6 microns MMAD and preferably from about 3 to about 5 microns MMAD.

One inhalation system that is suitable for practicing the current invention is an inhalation system that comprises a compressor-driven jet nebulizer that controls the patient's breathing pattern during the inspiration phase. This system is highly effective for inhalation therapy requiring deposition of the aerosol into the lower lungs. During the inhalation, the system controls number of breaths, flow rate and inspirational volume. This ability to control these three parameters assure that the patient is given a correct dose.

The inhalation system or device may further comprise an electronic means for storing an individualized treatment protocol. The treatment protocol may include such parameters as individual's lung function measurements, optimum breathing pattern, desired drug dose to maintain or restore patients vital capacity (VC), expiratory resting volume (ERV) and forced expiratory volume per one second (FEV1). These parameters may be individualized and stored on an appropriate storage means, such as the so-called Smart Card, which may also be used to transfer this information to the inhalation system during treatment and to record and store the information on how every aerosol administration was carried such as to reveal possible procedural errors.

The Smart Card system may hold more than one treatment configuration and is fully encrypted. The Smart Card system is disclosed in the co-pending US patent application 2001/0037806 A1, published on Nov. 8, 2001, herein incorporated by reference in its entirety. An appropriate nebulizing system is disclosed in the U.S. Pat. No. 6,606,989, herein incorporated by reference.

A similar but modified inhalation system further comprises, as a core element, a circular perforated membrane, that may be set to vibrate by a piezo-electric actuator. The vibrating motion of the membrane generates an alternating pressure that forces the nebulizing solution through a microarray of perforation in the membrane thus creating a fine aerosol having defined particle sizes. This system may similarly equipped with electronic means comprising the Smart Card, as described above. This system is known under the trade name AKITA$^2$ APIXNEB Inhalation System.

Another modification of the inhalation system that can be used for practicing the current invention is the nebulizer that is triggered by the negative trigger pressure detected by a pressure sensor. This nebulizer comprises a compressor that provides a constant inhalation flow rate of 12 liters/minute during inspiration. This system has controlled flow, volume and nebulization timing. The Smart Card settings include inhalation volume, inhalation time per breath, nebulization time per one breath. This system is known under the trade name AKITA JET Inhalation System. Other inhalation devices and systems that may be conveniently used or modified for use by the current invention are disclosed in the U.S. Pat. Nos. 6,401,710 B1, 6,463,929 B1, 6,571,791 B2, 6,681,762 B1 and 7,077,125 B2 or in published applications 2006/0201499 A1 and 2007/0006883 A1, all herein incorporated by reference.

A further inhalation system that is suitable for practicing the current invention is a breath actuated nebulizer. This nebulizer is characterized by a passive flow and active volume control. Typically, it comprises a single use aerosol generator and a multi-use control device. The device consists of an inhaler that is connected with a control unit. Inhaler itself is connected with nebulizer where the inhalable corticosteroid is nebulized into predetermined particles having sizes predominantly in the range from about 2 to about 6 μm, preferably between 3 and 5 μm using an aerosol generator. The filling volume of the nebulizer is approximately 4 ml. The aerosol generator is activated by pressure detection and is only activated during inspiration phase when the patient is inhaling the aerosolized corticosteroid. The pressure detection is controlled electronically.

This device is further equipped with a means to permit administration of particle-free air, to permit the administration of an aerosolized inhalable corticosteroid, and to permit the second administration of the particle-free air, each for a preselected time and volume, wherein the cumulative time for these three time intervals correspond to one inspiration time. The time for each of the interval corresponds to from about 1 millisecond to about 10 sec, preferably from about 200 millisecond to about 5 seconds.

The inhaler has an integrated flow and volume limited to about 15 liters/minute flow at a pressure of about 10 mbar or lower. When the underpressure at the mouthpiece is below 5 mbar, the flow rate is limited by a mechanical valve. The mechanical valve regulates the flow rate by a adjusting the cross section area. The unit is preset to a volume per one breath. One breath is set to be a time when one inspiration and one expiration occurs. After each inspiration time, the inspiration flow is blocked and expiration allowed. The inspiration flow is restored again for the next inspiration time during the next breath. This device has various electronic components that permits its preprogramming and individualization meeting requirements of the individual asthmatic patients.

An exemplary device is disclosed in the pending patent application Ser. No. 12/183,747, filed on Jul. 31, 2008, herein incorporated by reference. The device may be advantageously modified to provide a wide variety of variable conditions that may be easily individualized for patient's need. The modified device and method for its use is disclosed in the U.S. application Ser. No. 12/204,037, herein incorporated by reference in its entirety.

A double-blind, randomized, placebo-controlled phase II clinical trial was initiated to evaluate the tolerability, safety and efficacy of a therapy according to the invention. A fluticasone suspension was administered using an AKITA inhalation system for control of breathing pattern in subjects with asthma requiring chronic oral corticosteroid treatment. The objective of the clinical study is to evaluate the tolerability and safety of high dose nebulized fluticasone delivered with AKITA device and to study the efficacy of high dose nebulized fluticasone in reducing the need for oral corticosteroid (OCS) therapy.

Asthma subjects were maintained on a chronic dose of oral corticosteroids. The total study period is 24 weeks. The study schedule included a 2-weeks screening period, a 2-weeks treatment and tolerability period, an 18-weeks treatment period, including a 14-weeks OCS taper period with 7 downward tapering steps, and a follow-up visit 2 weeks after the last dose of study drug. All subjects were provided with oral prednisone to use for the duration of study participation.

One hundred or one hundred and twenty subjects (50 or 60 per treatment group) at approximately 25 asthma centers in three countries were assigned randomly to treatment with either high dose nebulized fluticasone or placebo administered BID. 4 mg fluticasone suspension (2 mL of 2 mg/mL fluticasone suspension) or matching placebo (2 mL of 0.9% sterile, normal saline in suspension) were delivered via the AKITA device using a jet nebulizer twice daily.

Enrolled subjects were older than 12 years and younger than 75 years of age and exhibited a FEV1 from 30% to 90% of predicted (pre-albuterol treatment). They have been treated with inhaled and oral corticosteroids for more than 6 months. The average daily dose of OCS at enrolment was within 5 to 70 mg of prednisone equivalent.

The study endpoint evaluation included the determination of reduction of OCS (oral corticosteroid, e.g. prednisone), improvement of asthma control, pulmonary function (FEV1), and reduction of pulmonary inflammation determined by amount of exhaled nitric oxide.

EXAMPLE 1

This example describes a therapy according to the invention, using a fluticasone composition and an AKITA device adapted to carry out the invention. The study was performed at the Davos Pulmonary Clinic. More than one hundred patients suffering from severe asthma that had been chronically maintained on oral corticosteroids were now being treated by once daily inhalation of high dose fluticasone (2000 μg fluticasone filled dose), using the AKITA system. Patients were selected on the basis of their need for OCS, and on the basis of poor symptom control. All patients had previously been treated with both inhaled corticosteroid/beta agonist combinations using meter dose inhalers and dry powder inhalers and oral steroids, at an average of 22.9 mg/day prednisolone or equivalents. None of the patients had adequate control of asthma symptoms and adequate pulmonary functions as determined by FEV1.

The treatment phase was about 1 to 9 weeks, with 3 weeks on average, under in-house conditions, as a once daily inhalation of fluticasone 2000 μg, in an open-label, uncontrolled fashion. Of the nominal, filled dose of 2000 μg, an approximate 500-700 μg reached the central lungs, with a similar amount remaining in the nebulizer. The remaining, small amount remained in the oropharynx or was exhaled.

The treatment duration for the 112 patients analyzed for 2007 was 7 to 53 days. Following outcome parameters were determined: Pulmonary function (FEV1), exhaled nitric oxide (FeNO), oral corticosteroid dose, and asthma control. On average, the daily treatment was applied for 22 days (range 7 to 53 days), while patients were hospitalized and monitored.

The outcome of the study was unexpected and surprising. Asthma control was achieved rapidly and consistently during treatment, while oral corticosteroids were reduced. Specifically, both the FEV1 and reduction of oral steroids showed highly significant changes versus baseline, $p<0.0001$). The daily intake of oral corticosteroids was reduced from a mean of 22.9 mg to 15.6 mg. The average FEV1 improved by 17.2% (or 340 ml). The oral steroids were reduced by 7.3 mg (33.2% reduction) on average. In addition, the pulmonary inflammation, as measured by exhaled nitric oxide, was reduced by 44.5% ($p<0.0001$). The use and handling of the AKITA nebulizing device for daily inhalation was well accepted by the patients and contributed to protocol compliance.

The invention claimed is:

1. A method for treatment of a patient having severe and uncontrolled asthma, said method comprising:

administering to the patient an inhalable corticosteroid, as a nebulized aerosol in a gas phase, wherein (a) the nebulized aerosol is administered during the inhalation phase of the patient at a rate of not more than about 20 liters per minute;

(b) a total volume of at least about 0.4 liters of gas phase is administered per inhalation phase, said gas phase including the nebulized aerosol and aerosol-free air; and (c) not more than about 150 milliliters of aerosol-free air is administered before administering the nebulized aerosol; and wherein said method further includes the oral administration of a glucocorticoid at a daily dose which is not higher than about 40 milligrams of prednisolone or an equipotent dose of another glucocorticoid.

2. The method of claim 1, wherein the glucocorticoid is selected from the group consisting of fluticasone propionate, budesonide, beclomethasone dipropionate, ciclesonide, flunisolide, mometasone furoate, and triamcinolone acetonide.

3. The method of claim 1, wherein the orally administered glucocorticoid is selected from the group consisting of hydrocortisone, dexamethasone, prednisone, prednisolone, and methylprednisolone.

4. The method of claim 1, wherein the daily dose of the orally administered glucocorticoid is decreased during therapy by at least 30% relative to an initial daily dose.

5. The method of claim 4, wherein the daily dose of the orally administered glucocorticoid is decreased to zero during the therapy.

6. A method for treatment of a patient having severe and uncontrollable asthma requiring a concurrent treatment with oral corticosteroids, said method comprising administering to the patient in need thereof an inhalable treatment comprising administration of an inhalable corticosteroid selected from the group consisting of fluticasone, beclomethasone dipropionate, budesonide, mometasone furoate, ciclesonide, flunisolide and triamcinolone acetonide as an aerosol comprising said corticosteroid in amount from about 400 to about 4000 micrograms, using a nebulizer device able to administer an aerosolized corticosteroid into lower lungs with overpressure of 40 mbar or less, wherein said overpressure results in a larger than 200 micrograms deposition of said corticosteroid into the lower lungs, and wherein said inhalable treatment results in reduction of at least 30% of oral steroids requirement and reduction of oropharyngeal side effects.

7. A method for treatment of a patient having severe and uncontrollable asthma requiring a concurrent treatment with oral corticosteroids, said method comprising a treatment protocol comprising administering to a patient in need thereof an inhalable treatment comprising administration of an inhalable corticosteroid selected from the group consisting of fluticasone, beclomethasone dipropionate, budesonide, mometasone furoate, ciclesonide, flunisolide and triamcinolone acetonide as an aerosol comprising said corticosteroid in amount from about 400 to about 4000 micrograms, wherein said aerosol is administered during an inspiration time comprising three predefined periods, wherein in the first period lasting from about 1 millisecond to about 1 second, an aerosolized particle-free air is administered at a preset flow rate and at a preset volume;

wherein in the second period lasting from about 0.1 to about 5 seconds, an aerosolized corticosteroid is administered at a preset flow rate and at a preset volume; wherein in the third period, lasting from about 1 millisecond to about 10 seconds, an aerosolized particle-free air is administered at a preset flow rate and at a preset volume; wherein after the third period, the patient is instructed to stop inhaling and exhale; wherein said protocol is repeated for about 6 to about 10 minutes or less; and wherein said treatment results in a larger than 200 micrograms deposition of said corticosteroid into the lower lungs.

8. The method of claim 2, wherein the orally administered glucocorticoid is selected from the group consisting of hydrocortisone, dexamethasone, prednisone, prednisolone, and methylprednisolone.

9. The method of claim 2, wherein the daily dose of the orally administered glucocorticoid is decreased during therapy by at least 30% relative to an initial daily dose.

10. The method of claim 3, wherein the daily dose of the orally administered glucocorticoid is decreased during therapy by at least 30% relative to an initial daily dose.

11. The method of claim 1 wherein an inhalation device is employed to administer to the patient the inhalable corticosteroid.

12. The method of claim 11, wherein the inhalation device is adapted to emit, per inhalation phase, a total volume of gas phase in the range from about 0.4 to about 1.4 liters, which total volume is selected on the basis of the patient's inhalation capacity or of the patient's actual and predicted forced expiratory volume in one second.

13. The method of claim 11, wherein the inhalation device is adapted to generate a nebulized aerosol having a mass median aerodynamic diameter (MMAD) from about 3 to about 5 micrometers.

14. The method of claim 11, wherein the inhalation device is adapted to emit, per inhalation phase, a total volume of gas phase in the range from about 0.4 to about 2 liters, which total volume is selected on the basis of the patient's inhalation capacity or of the patient's actual and predicted forced expiratory volume in one second.

15. The method of claim 11, wherein the inhalation device is adapted to generate a nebulized aerosol having a mass median aerodynamic diameter (MMAD) from about 2 to about 6 micrometers.

16. The method of claim 11, wherein the inhalation device is adapted to emit the nebulized aerosol during the inhalation phase of the patient at an overpressure of up to about 40 mbar.

17. The method of claim 16, wherein the overpressure is maintained during the inhalation phase at at least about 1 mbar.

18. The method of claim 11, wherein the inhalation device is adapted to emit the gas phase only after breath actuation by the patient.

19. The method of claim 11, wherein the inhalation device is adapted to emit, per inhalation phase, from about 200 to about 3,000 milliliters of nebulized aerosol.

20. The method of claim 19, wherein the inhalation device is adapted to emit the nebulized aerosol at a rate of not more than about 300 milliliters per second.

21. The method of claim 19, wherein the inhalation device is adapted to emit, per inhalation phase, from about 200 to about 500 milliliters of aerosol-free air after emitting the nebulized aerosol.

22. The method of claim 21, wherein the inhalation device is adapted to emit the nebulized aerosol at a rate of not more than 250 milliliters per second.

* * * * *